United States Patent [19]

Wyrick et al.

[11] Patent Number: 4,499,303
[45] Date of Patent: Feb. 12, 1985

[54] ANTIHYPERLIPIDEMIC N-BENZOYLSULFAMATES, N-BENZYLSULFAMATES AND BENZYLSULFONAMIDES

[75] Inventors: Steven D. Wyrick, Durham; Iris H. Hall; Agnes Dubey, both of Chapel Hill, all of N.C.

[73] Assignee: Research Corporation, New York, N.Y.

[21] Appl. No.: 536,218

[22] Filed: Sep. 27, 1983

[51] Int. Cl.³ .................. C07C 143/74; C07C 143/78
[52] U.S. Cl. ..................................... 514/605; 564/90; 514/617
[58] Field of Search ................... 564/90; 424/320, 321

[56] References Cited

U.S. PATENT DOCUMENTS

| | | | |
|---|---|---|---|
| 2,373,299 | 4/1945 | Dougherty et al. | 564/90 X |
| 3,400,152 | 9/1968 | Block et al. | 564/90 X |
| 3,983,107 | 9/1976 | Holland | 564/90 X |
| 4,113,463 | 9/1978 | Oshio et al. | 564/90 X |
| 4,310,545 | 1/1982 | Shepherd | 564/90 X |

Primary Examiner—Paul F. Shaver
Attorney, Agent, or Firm—Scully, Scott, Murphy & Presser

[57] ABSTRACT

This invention relates to novel N-benzoylsulfamates, N-benzylsulfamates and benzylsulfonamides and pharmacologically acceptable salts thereof, a method for lowering serum levels in mammals by administration of said compounds, and pharmaceutical compositions thereof.

16 Claims, No Drawings

ANTIHYPERLIPIDEMIC N-BENZOYLSULFAMATES, N-BENZYLSULFAMATES AND BENZYLSULFONAMIDES

The invention described herein was made in the course of work under a grant or award sponsored in part by the National Institute of Dental Research.

BRIEF SUMMARY OF THE INVENTION

This invention relates to new organic compounds and more particularly is concerned with novel N-benzoyl and N-benzylsulfamates which may be represented by the following general formula:

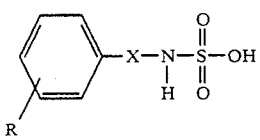

(I)

wherein X is selected from the group consisting of C=O and $CH_2$ and R is selected from the group consisting of hydrogen, halogen, lower alkyl, lower alkoxy and lower acyl; and benzylsulfonamides which may be represented by the following general formula:

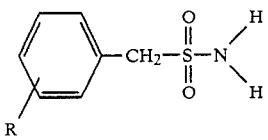

(II)

wherein R is selected from the group consisting of hydrogen, halogen, lower alkyl, lower alkoxy and lower acyl. The term lower alkyl is meant to include radicals having from 1–6 carbon atoms.

The novel compounds, preferably in the form of their salts, are highly useful in the treatment of hyperlipidemia, a condition associated with cholesterol, phospholipid and/or triglyceride blood levels. This condition is associated with a number of diseases, one of the most serious being atherosclerosis. In general, both series of the sulfamates and sulfonamides described above significantly lower serum cholesterol and triglyceride levels in mice. The compounds are non-mutagenic, show no acute toxicity or impaired liver or kidney function in male mice and are chemically stable both dry and in aqueous solution over a pH range of 3.5–7.4. While both series of sulfamates and sulfonamides lower serum cholesterol and triglyceride levels, the sulfamates are relatively more potent with regard to decreasing cholesterol levels while the sulfonamides are more effective in lowering serum triglyceride levels in mice.

DETAILED DESCRIPTION OF THE INVENTION

While the novel compounds of the present invention may be synthesized, in low yield, using several prior art processes, it has been found herein that improved yields can be provided by employing certain novel procedures.

For example, the N-benzoyl and N-benzylsulfamic acids and salts of the present invention are prepared in improved yield in accordance with the following reaction scheme:

SCHEME I

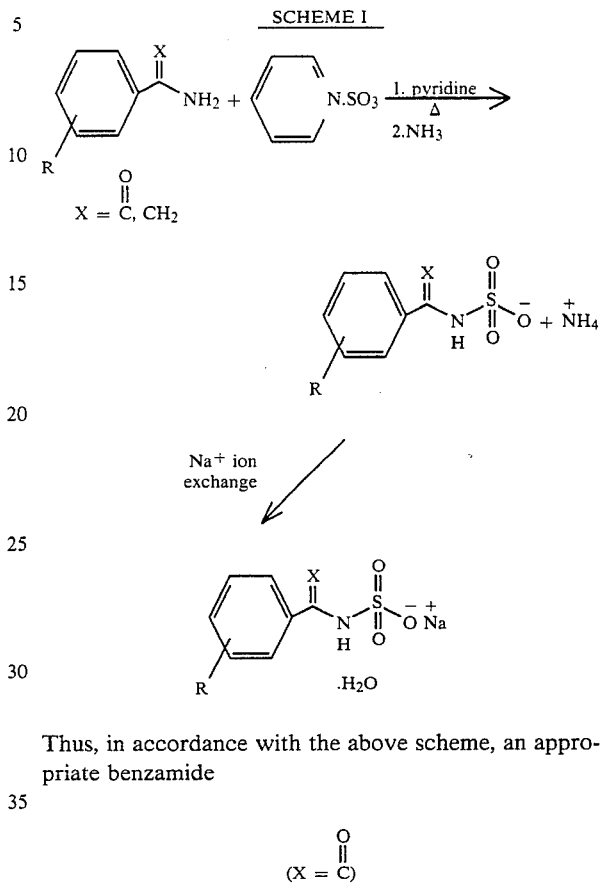

Thus, in accordance with the above scheme, an appropriate benzamide $$(X = \overset{O}{\underset{\|}{C}})$$

or benzylamine ($X=CH_2$) is contacted with pyridine sulfurtrioxide in pyridine solution for a period of time, e.g. about 3 to about 5 hours, at an elevated temperature, e.g. 80°–90° C. The crude product, isolated as the ammonium salt, is converted to the sodium salt by ion exchange chromatography.

The starting benzoyl amides can be prepared by conventional prior art procedures, e.g. reacting the appropriate benzoyl chloride with cold $NH_4OH$, the product filtered, dried and recrystallized from ethanol —$H_2O$. Benzyl amines are readily available or may be prepared by treatment of the corresponding benzyl bromide with ammonia.

The N-benzylsulfonamides of the present invention can be prepared employing the following reaction scheme II:

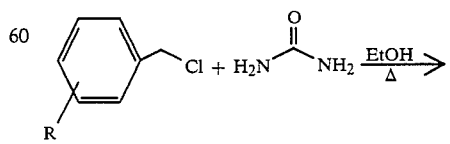

R = H; o, m, p-Cl;
o, m, p-$NO_2$

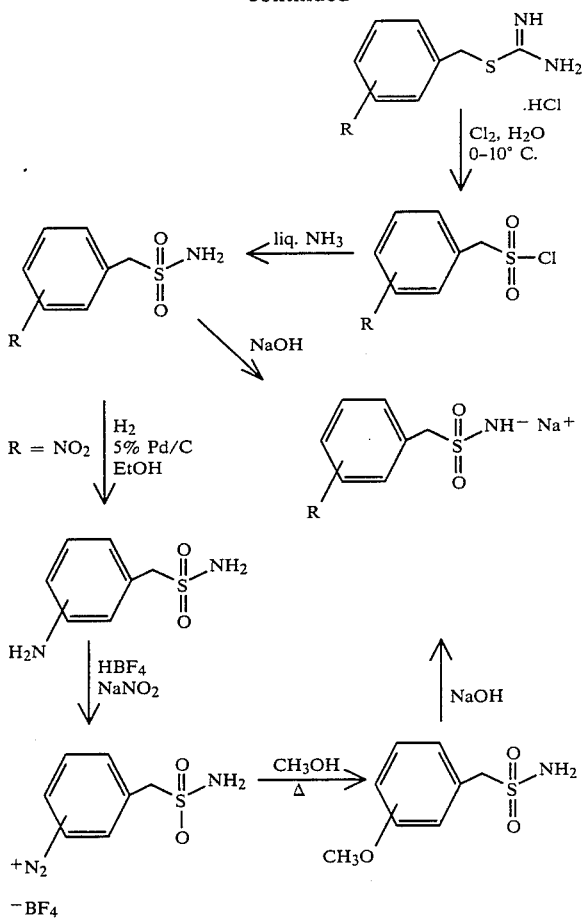

As illustrated, the N-benzylsulfonamides are prepared from the corresponding sulfonyl chlorides which are obtained by treatment of the benzylisothioureas with chlorine gas at a temperature of about 0°–10° C. The desired salts are formed by treatment with the appropriate metal hydroxide, such as sodium hydroxide. This procedure is satisfactory for derivatives wherein R is an electron withdrawing group or hydrogen. Strong electron releasing substituents, such as —OCH₃, induce chlorination of the aromatic ring during con-version to the sulfonyl chloride. This problem is circumvented by obtaining the nitrobenzylsulfonamide, catalytic reduction of the nitro substituent and the introduction of the electron releasing substituent (e.g. OCH₃) via the diazonium tetrafluoroborate salt, as illustrated also.

As indicated above, the novel compounds have been shown to possess antihyperlipidemic activity as determined by animal experiments.

The test compounds were administered daily to CF₁ male mice (average weight 28 grams) as a 1% carboxymethylcellulose suspension at 20 mg/kg/day I.P. On days 9 and 16, blood was obtained by tail bleeding and after centrifugation to obtain serum, 25 μl samples were assayed for total cholesterol by the procedure of Ness at al. Clin. Chem. Acta, 10, 229(1964). Serum triglycerides were assayed using the commercially available Bio-Dynamics/bmc Triglyceride Kit on blood collected on the 16th day. By comparison to standards, the mg% of cholesterol and mg/dl of triglycerides were calculated. Treated values are expressed as percent of control.

In these tests a compound is considered to have hypolipidemic activity if it depresses serum sterol levels 15% or more below that of the controls, and/or depresses triglyceride levels by 25% or more below that of the controls. The results of this test with representative compounds of the present invention appear in Table 1 below.

TABLE I

Antihyperlipidemic Effects of Test Compounds in CF₁ Male Mice

| Compound No. (N = 6) | % Control | | |
|---|---|---|---|
| | Serum Cholesterol | | Serum Triglycerides |
| | Day 9 | Day 16 | Day 16 |
| 1 | 63 ± 6 | 60 ± 7 | 65 ± 8 |
| 2 | 57 ± 5 | 52 ± 6 | 55 ± 7 |
| 3 | 72 ± 5 | 64 ± 6 | 97 ± 7 |
| 4 | 78 ± 6 | 51 ± 5 | 86 ± 8 |
| 5 | 86 ± 7 | 72 ± 5 | 80 ± 7 |
| 7 | 74 ± 6 | 57 ± 5 | 70 ± 6 |
| 8 | 75 ± 4 | 73 ± 7 | 88 ± 3 |
| 9 | 70 ± 3 | 63 ± 3 | 82 ± 4 |
| 10 | 95 ± 3 | 72 ± 4 | 69 ± 6 |
| 11 | 90 ± 6 | 77 ± 6 | 49 ± 8 |
| 12 | 88 ± 4 | 87 ± 2 | 91 ± 9 |
| 13 | 94 ± 7 | 88 ± 2 | 97 ± 8 |
| 14 | 84 ± 8 | 78 ± 2 | 75 ± 2 |
| 15 | 94 ± 2 | 93 ± 4 | 79 ± 7 |
| 16 | 99 ± 8 | 73 ± 6 | 52 ± 6 |
| 17 | 69 ± 4 | 68 ± 7 | 58 ± 6 |
| 18 | 84 ± 6 | 79 ± 7 | 42 ± 4 |
| 19 | 74 ± 8 | 70 ± 5 | 76 ± 7 |
| 20 | 95 ± 8 | 75 ± 5 | 42 ± 3 |
| 21 | 92 ± 7 | 77 ± 5 | 71 ± 5 |
| 22 | 94 ± 7 | 78 ± 8 | 48 ± 4 |
| Saccharin | 77 ± 6 | 68 ± 7 | 48 ± 6 |
| Clofibrate | 98 ± 7 | 97 ± 9 | 95 ± 7 |
| 1% CMC | 100 ± 7 | 100 ± 6 | 100 ± 7 |

The test compounds are negative in the Ames mutagenic assay, demonstrate no acute toxicity or impaired liver and kidney function and are chemically stable.

Of the compounds of the present invention, the N-benzoylsulfamides appear to be the more potent antihypercholesteremics, the o- and p-chloro derivatives being the most active. As indicated in Table I, electron withdrawing substituents on the aromatic ring lend slightly greater activity to the series than do electron releasing substituents and activity decreases somewhat with increasing substituent size. In general, activity within the series does not appear to be heavily dependent upon the size, electronic properties or lipophilicity of the aromatic substituents as the unsubstituted prototype is also quite active. A significantly greater structural dependence within this series resides in the side chain requirement for the carbonyl function. By comparison of the p—Cl, o—Cl, p—OCH₃ and unsubstituted derivatives with their carbonyl reduced counterparts among the N-benzylsulfamates, it is evident that antihypercholesteremic activity is markedly reduced in the absence of the carbonyl function. This structural requirement for antihyperlipidemic activity has also been noted for saccharin as well as other imides. Serum triglyceride levels are moderately reduced by the N-benzoyl sulfamates with the exception of the p—Cl and p-isopropyl derivative which lower serum triglyceride levels 55±7% and 49±8% of control values, respectively, by day 16. As in the case of antihypercholesteremic activity, the dependence on the presence of the side chain carbonyl for antihypertriglyceridemic activity appears evident when comparing compounds 1, 2 and 7 with 12, 15 and 13, respectively. However, N-benzylsulfamate 14 shows increased antihyertriglyceridemic activity compared to N-benzoylsulfamate 4. Each of the N-benzoylsulfamates shows greater antihypercholesteremic activity than clofibrate, and compounds 1, 2, 3, 4 and 7 are more active than saccharin in lowering serum cholesterol levels but less active in lowering triglyceride levels.

Within the benzylsulfonamide series, the o—OCH$_3$ derivative 17 was the most active antihypercholesteremic, being equal in activity to saccharin. In general, moderate antihypercholesteremic activity is displayed by this series whereas, antihypertriglyceridemic activity surpasses that of the N-benzoylfulfamates and clofibrate. The p—Cl derivative 22 is equally active with saccharin in this respect. Compounds 18 and 20 are more active than saccharin, lowering serum triglyceride levels to 42% of control values. Comparing the activity of 16, 18, 20, 22 the most active antihypertriglyceridemics in the series, no dependence on substituent parameters is evident.

Of the series of compounds tested thus far, N-(p-chlorobenzoyl)-sulfamate and (o-chlorobenzyl)-sulfonamide appear to be of the most interest. N-(p-chlorobenzoyl)-sulfamic acid sodium salt at 20 mg/kg/day, I.P. lowered serum cholesterol levels 48% and serum triglyceride levels 45% after 16 days dosing. (o-Chlorobenzyl)sulfonamide was also observed to be a potent hypolipidemic agent in rodents reducing serum cholesterol levels 71% and triglyceride levels 49% at 60/mg/kg/day. This compound is effective both in normal and hyperlipidemic mice and is active both orally an intraperitonally.

The compounds of this invention are thus useful as hypolipidemic compounds in mammals when administered in amounts ranging from about 10 mg/per/kg to about 40 mg/per/kg of body weight per day. Thus, the daily dosage of the active compounds employed for a subject of about 70 kg. body weight is about 700 mg to about 2800 mg administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compounds may be administered in any convenient manner such as by the oral, intravenous, intramuscular, or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that dosage unit form contains between about 700 and 2800 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, aliginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compounds may also be administered parenterally or intraperitoneally. Solutions of the active compound as a free acid or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The invention will be described in greater detail in conjunction with the following specific examples.

EXAMPLES 1-15

N-Benzoyl- and N-Benzylsulfamic Acid Sodium Salts

As set forth in Reaction Scheme I, the appropriate benzamide or benzylamine (5.0 g) and 1.1 equivalents of pyridine sulfurtrioxide complex are dissolved with warming in 50 ml of dry pyridine under $N_2$. The reaction is stirred at 80°–90° C. for 3–5 hours at which time TLC (ethyl acetate-acetic acid-$H_2O$ 6:3:1) showed no further reaction. The solution is cooled in ice and the excess precipitated pyr.$SO_3$ filtered off and washed with cold pyridine. The filtrate is treated with gaseous ammonia for 10 min, concentrated in vacuo to about one-third its volume and poured into ether-methanol 4:1 with vigorous stirring. The precipitated ammonium salt is collected, washed with ether and dried. Conversion to the sodium salt is effected by dissolving the crude ammonium salt in the least amount of water (warming if necessary) followed by rapid elution with $H_2O$ from a column of $Na^+$ form ion exchange resin. The aqueous eluent is concentrated in vacuo until crystallization of the product begins. The mixture is then stored at 3°–5° C. to complete crystallization. The product is collected, washed with cold $H_2O$ and vacuum dried to afford the product as the sodium salt monohydrate. Those derivatives which are extremely $H_2O$ soluble are recrystallized from methanol. Each compound begins to melt at about 100° C. and finishes melting above 200° C. The compounds so prepared are listed in Table II.

TABLE II

N—Benzoyl- and N—Benzylsulfamic Acid Sodium Salts

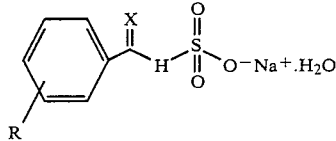

| Compound Number | R | X | Formula | Elemental Analysis | C | H | N |
|---|---|---|---|---|---|---|---|
| 1 | p-OCH$_3$ | O | C$_8$H$_{10}$NO$_6$SNa | calculated: | 35.43 | 3.69 | 5.17 |
|   |   |   |   | found: | 35.09 | 3.51 | 5.24 |
| 2 | p-Cl | O | C$_7$H$_7$ClNO$_5$SNa | calculated: | 30.49 | 2.54 | 5.08 |
|   |   |   |   | found: | 30.49 | 2.42 | 5.16 |
| 3 | m-Cl | O | C$_7$H$_7$ClNO$_5$SNa | calculated: | 30.49 | 2.54 | 5.08 |
|   |   |   |   | found: | 30.49 | 2.50 | 5.12 |
| 4 | o-Cl | O | C$_7$H$_7$ClNO$_5$SNa | calculated: | 30.49 | 2.54 | 5.08 |
|   |   |   |   | found: | 30.25 | 2.74 | 4.88 |
| 5 | m-OCH$_3$ | O | C$_8$H$_{10}$NO$_6$SNa | calculated: | 35.43 | 3.69 | 5.17 |
|   |   |   |   | found: | 35.19 | 3.57 | 5.29 |
| 6 | o-OCH$_3$ | O | C$_8$H$_{10}$NO$_6$SNa | calculated: | 35.43 | 3.69 | 5.17 |
|   |   |   |   | found: | 35.47 | 3.66 | 5.22 |
| 7 | H | O | C$_7$H$_8$NO$_5$SNa | calculated: | 34.85 | 3.32 | 5.81 |
|   |   |   |   | found: | 34.67 | 3.31 | 5.94 |
| 8 | p-Br | O | C$_7$H$_7$BrNO$_5$SNa | calculated: | 27.29 | 2.05 |  |
|   |   |   |   | found | 27.27 | 2.19 |  |
| 9 | p-CH$_3$ | O | C$_8$H$_{10}$NO$_5$SNa | calculated: | 37.67 | 3.92 |  |
|   |   |   |   | found | 37.62 | 3.78 |  |
| 10 | p—CH$_3$C(=O) | O | C$_9$H$_{10}$NO$_6$SNa | calculated: | 37.00 | 3.76 |  |
|   |   |   |   | found | 37.19 | 3.87 |  |
| 11 | p-i-C$_3$H$_7$ | O | C$_{10}$H$_{14}$NO$_5$SNa | calculated: | 42.42 | 4.94 |  |
|   |   |   |   | found: | 42.45 | 5.09 |  |
| 12 | p-OCH$_3$ | H$_2$ | C$_8$H$_{10}$O$_4$SNNa | calculated: | 40.17 | 4.18 | 5.86 |
|   |   |   |   | found: | 40.18 | 4.19 | 5.88 |
| 13 | H | H$_2$ | C$_7$H$_8$O$_3$SNNa | calculated: | 40.19 | 3.83 | 6.70 |
|   |   |   |   | found: | 40.02 | 3.76 | 6.76 |
| 14 | o-Cl | H$_2$ | C$_7$H$_7$O$_3$ClSNNa | calculated: | 34.50 | 2.87 | 5.75 |

TABLE II-continued
N—Benzoyl- and N—Benzylsulfamic Acid Sodium Salts

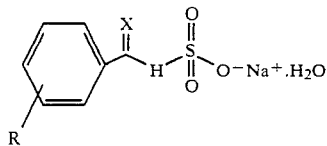

| Compound Number | R | X | Formula | Elemental Analysis | C | H | N |
|---|---|---|---|---|---|---|---|
| 15 | p-Cl | H$_2$ | C$_7$H$_7$O$_3$ClSNNa | found: | 34.61 | 2.71 | 5.91 |
| | | | | calculated: | 34.50 | 2.87 | 5.75 |
| | | | | found: | 34.54 | 2.78 | 5.77 |

EXAMPLES 16–22
Substituted Benzylsulfonamides

As set forth in Reaction Scheme II the starting benzyl chlorides can be prepared by conventional routes, e.g. by reacting the appropriate benzyl alcohol with thionyl chloride in pyridine at room temperature and distilling off the product. The S-(substituted benzyl)-isothiourea hydrochlorides are prepared according to the prior art by reacting the appropriate benzyl chloride e.g. 0.05 to 0.2 mole with one equivalent of thiourea and stirring under reflux in absolute ethanol for several hours. The product crystallizes upon cooling. Continuing the process, the appropriate S-(substituted benzyl)-isothiourea hydrochloride is dissolved in water (e.g. 600–700 ml. per 0.2 mole depending upon solubility) and cooled in ice to 0°–10° C. The solution is then treated with gaseous chlorine for 30 minutes while maintaining the temperature below about 10° C. The solid or oily product is extracted with ether, the ether extracts dried with, e.g. sodium sulfate, and evaporated in vacuo to afford the substituted benzylsulfonyl chloride which is sufficiently pure for conversion to the sulfonamide.

The resulting appropriate benzylsulfonyl chloride is dissolved in liquid ammonia. The liquid ammonia may be provided, e.g., by condensing ammonia gas with a dry-ice acetone condenser. The resulting solution is kept at e.g. −78° for 1 hour and then the excess ammonia is allowed to evaporate. The residue is dissolved in chloroform and filtered to remove NH$_4$Cl. The filtrate is dried with e.g. Na$_2$SO$_4$ and evaporated to afford the crude sulfonamide which is either recrystallized from ethanol or column chromatography e.g. Silica Gel 60, CH$_2$Cl$_2$-methanol (9:1). The pure product is converted to the appropriate salt, e.g. sodium salt, by treating an ethanolic solution with 1.0 equivalent of 12M aqueous NaOH. Upon cooling, the precipitated salt is collected and dried in vacuo. The products are obtained in varying degrees of hydration. Melting points are generally greater than 250° C.

In the one case of substituents having strong electron releasing capabilities, a solution of the appropriate nitro substituted benzylsulfonamide (prior to sodium salt formation) is dissolved in absolute ethanol (1600 ml per 34 g of substrate) and shaken for 6–8 hours at 40° C. on a Parr apparatus with 1.0 g of 5% Pd on charcoal under 60 psi of H$_2$. When the reaction is complete, the catalyst is removed by filtration and filtrate evaporated in vacuo to afford an essentially quantitative yield of the aniline compound.

For the diazotiazation of the aminobenzylsulfonamides a three-neck reaction flask equipped with mechanical stirrer and addition funnel is charged with 9.0–10.0 g of the aniline compound. A 24% solution of fluoroboric acid (0.121 moles) is added dropwise with cooling in an ice bath. The resulting solution is maintained at 0°–5° C. while an aqueous solution of NaNO$_2$ (0.048 mole) is added dropwise with stirring, followed by stirring at 0°–5° C. for 1.5 hr. The precipitated diazonium fluoroborate salt is collected, washed on the filter with 5% HBF$_4$, cold methanol, then cold ether and dried in vacuo to afford light tan crystals.

A solution of the above diazonium fluoroborate salt in methanol (1200 ml per 10 g) is heated to 50° C. for 5 hours in a flask open to the atmosphere. The orange solution is then evaporated to dryness in vacuo and the residue chromatographed on a column of silica gel 60 with CH$_2$Cl$_2$-acetone (9:1), (8:2) to afford the product which is converted to the sodium salt as described above.

The compounds so prepared are listed in Table III.

TABLE III
Benzylsulfonamide Sodium Salts

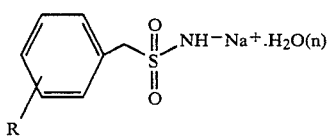

| Compound Number | R | (n) | Formula | Elemental Analysis | | C | | |
|---|---|---|---|---|---|---|---|---|
| 16 | o-Cl | 1 | C$_7$H$_7$ClNO$_2$SNa .H$_2$O | calculated: found: | | 34.24 34.34 | 3.66 3.52 | 5.70 5.80 |
| 17 | o-OCH$_3$ | 2 | C$_8$H$_{10}$NO$_3$SNa .2H$_2$O | calculated: found: | | 37.08 37.37 | 5.40 5.34 | 5.40 5.40 |
| 18 | m-OCH$_3$ | 1½ | C$_8$H$_{10}$NO$_3$SNa .1½ H$_2$O | calculated: found: | | 38.43 38.08 | 4.80 4.55 | 5.60 5.66 |
| 19 | p-OCH$_3$ | ½ | C$_8$H$_{10}$NO$_3$SNa | calculated: | | 41.39 | 4.74 | 6.03 |

TABLE III-continued
Benzylsulfonamide Sodium Salts

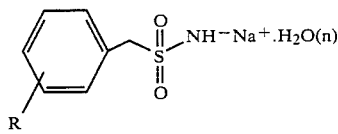

| Compound Number | R | (n) | Formula | Elemental Analysis | | | |
|---|---|---|---|---|---|---|---|
| | | | | | C | H | N |
| 20 | H | 1 | .½H₂O C₇H₈N S O₂Na .H₂O | found: calculated found: | 41.39 43.52 43.36 | 4.63 4.15 4.09 | 6.01 7.25 7.23 |
| 21 | m-Cl | 1 | C₇H₇ClNO₂SNa .H₂O | calculated: found: | 36.92 36.58 | 3.08 3.34 | 6.15 5.85 |
| 22 | p-Cl | 1 | C₇H₇ClNO₂SNa .H₂O | calculated: found: | 36.92 36.85 | 3.08 3.03 | 6.15 5.98 |

An advantageous characteristic feature of the compounds of the present invention is their ability to form salts. Suitable agents in the formation of salts include alkali metal hydroxides, alkali metal carbonates, alkali metal hydrides, alkali metal alkoxides, alkaline earth metal hydroxides, alkaline earth metal carbonates, alkaline earth metal hydrides and alkaline earth metal alkoxides. More specifically, hydroxides include sodium hydroxide, potassium hydroxide, alkoxides include sodium ethoxide and potassium ethoxide, hydrides such as sodium hydride; carbonates include potassium carbonate and sodium carbonate.

Although, when contemplating therapeutic use for a compound of the instant invention it is preferable to use a pharmaceutically-acceptable salt, salts other than these can be used for a variety of other purposes. Such purposes include isolating and purifying particular compounds, and interconverting pharmaceutically-acceptable salts with their non-salt counterparts.

What is claimed is:

1. A compound selected from the group consisting of those of the formula:

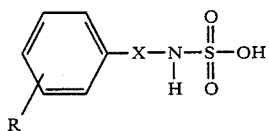

wherein X is selected from the group consisting of C=O and CH₂ and R is selected from the group consisting of hydrogen, halogen, lower alkyl, lower alkoxy and lower acyl and the pharmacologically acceptable salts thereof.

2. A compound according to claim 1 in association with a pharmaceutically acceptable carrier.

3. A compound selected from the group consisting of those of the formula:

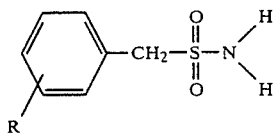

wherein R is selected from the group consisting of hydrogen, halogen, lower alkyl, lower alkoxy and lower acyl and the pharmacologically acceptable salts thereof.

4. A compound according to claim 3 in association with a pharmaceutically acceptable carrier.

5. A compound according to claim 1 wherein R is chloro.

6. A compound according to claim 3 wherein R is chloro.

7. A method of treating hyperlipidemia in a mammal comprising administering to said mammal an effective serum lipid-lowering amount of a compound of the formula:

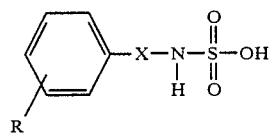

wherein X is selected from the group consisting of C=O and CH₂ and R is selected from the group consisting of hydrogen, halogen, lower alkyl, lower alkoxy and lower acyl or a pharmacologically acceptable salt thereof.

8. The method of claim 7 wherein the compound is administered to provide a daily dosage of from about 10 mg to about 40 mg per kg of body weight of said mammal.

9. The method of claim 7 wherein the compound is N-(p-chlorobenzoyl)-sulfamate or a pharmacologically acceptable salt thereof.

10. The method of claim 9 wherein the compound is in the sodium salt form.

11. A method of treating hyperlipidemia in a mammal comprising administering to said mammal an effective serum lipid-lowering amount of a compound of the formula:

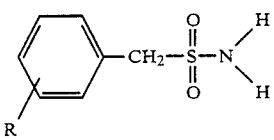

wherein R is selected from the group consisting of hydrogen, halogen, lower alkyl, lower alkoxy and lower acyl or a pharmacologically acceptable salt thereof.

12. The method of claim 11 wherein the compound is administered to provide a daily dosage of from about 10 mg to about 40 mg per kg of body weight of said mammal.

13. The method of claim 12 wherein the compound is (o-chlorobenzyl)-sulfonamide.

14. The method of claim 13 where the compound is in the sodium salt form.

15. A therapeutic composition in dosage unit form which is useful to lower serum lipids comprising a compound of the formula:

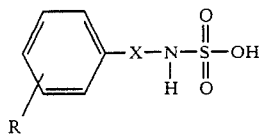   (I)

wherein X is selected from the group consisting of C=O and CH$_2$ and R is selected from the group consisting of hydrogen, halogen, lower alkyl, lower alkoxy and lower acyl or a pharmalogically acceptable salt thereof, in concentrations per dosage unit to provide a daily dosage of from about 700 mg to about 2800 mg in association with a pharmaceutically acceptable carrier.

16. A therapeutic composition in dosage unit form which is useful to lower serum lipids comprising a compound of the formula:

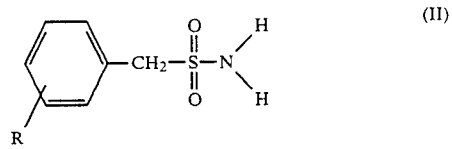   (II)

wherein R is selected from the group consisting of hydrogen, halogen, lower alkyl, lower alkoxy and lower acyl or a pharmacologically acceptable salt thereof, in concentrations per dosage unit to provide a daily dosage of from about 700 mg to about 2800 mg in association with a pharmaceutically acceptable carrier.

* * * * *